United States Patent [19]

Jamison et al.

[11] Patent Number: 5,086,646
[45] Date of Patent: Feb. 11, 1992

[54] APPARATUS AND METHOD FOR ANALYZING WELL FLUID SAG

[76] Inventors: Dale E. Jamison, 19911 Rustlewood Dr., Humble, Tex. 77338; William R. Clements, 16407 Southampton Dr., Spring, Tex. 77379

[21] Appl. No.: 405,899

[22] Filed: Sep. 12, 1989

[51] Int. Cl.⁵ .................. G01L 1/12; G01N 15/04
[52] U.S. Cl. ............................... 73/65; 73/61.4
[58] Field of Search ............. 73/53, 61 R, 61.4, 65, 73/153, 865.6, 866.4

[56] References Cited

U.S. PATENT DOCUMENTS

| | | | |
|---|---|---|---|
| 2,845,793 | 8/1958 | Cardwell, Jr. | 73/61.4 |
| 3,371,523 | 3/1968 | Crouch et al. | 73/65 |
| 3,470,735 | 10/1969 | Bradley | 73/865.6 X |
| 4,474,056 | 10/1984 | O'Brien et al. | 73/61.4 |

Primary Examiner—Charles A. Ruehl
Attorney, Agent, or Firm—Browning, Bushman, Anderson & Brookhart

[57] ABSTRACT

A method and apparatus for analyzing sag phenomena in well fluids wherein an elongate container containing a sample of a fluid to be tested is mounted at an angle with respect to vertical on a force responsive device which provides a measurable, variable indication of the center of mass of the container. The angle is chosen to correspond to that of a well deviation angle for which testing is to be done, and the sample may be subjected to heat and pressure to further simulate downhole conditions. The aforementioned indication provided by the force responsive device is repeatedly measured and functionally related to time.

52 Claims, 4 Drawing Sheets

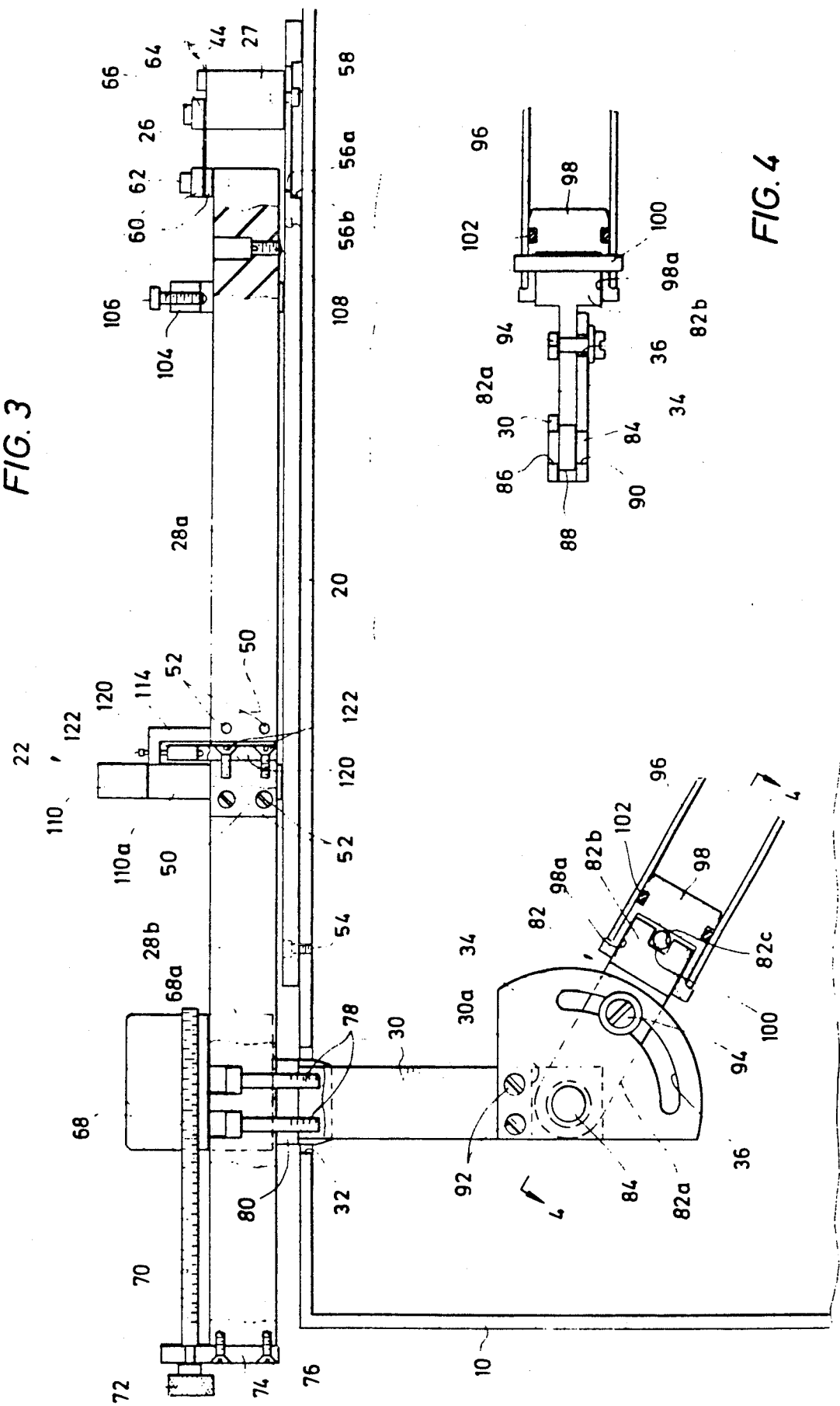

FIG. 8
FIG. 9
FIG. 10
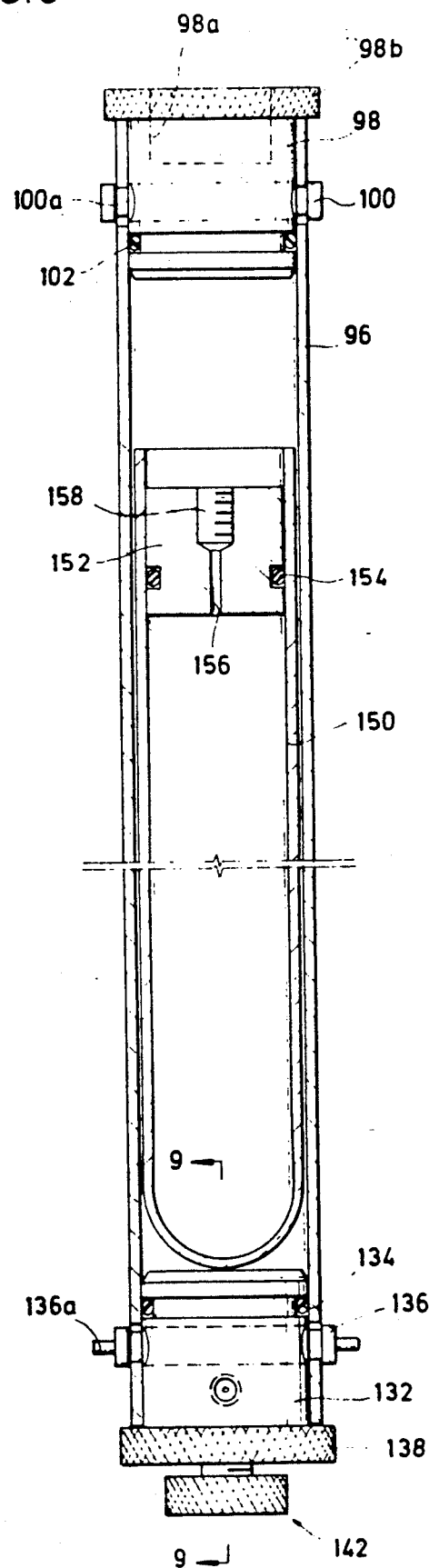
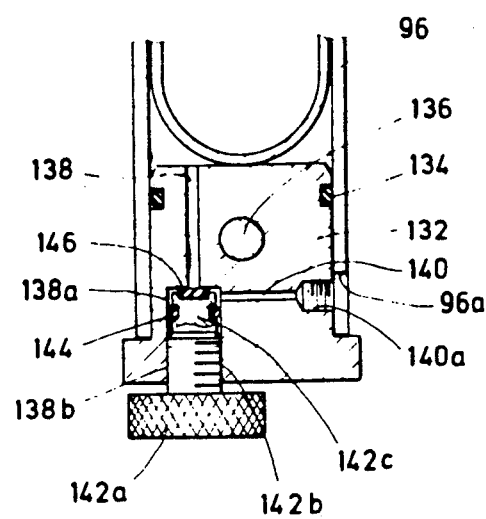
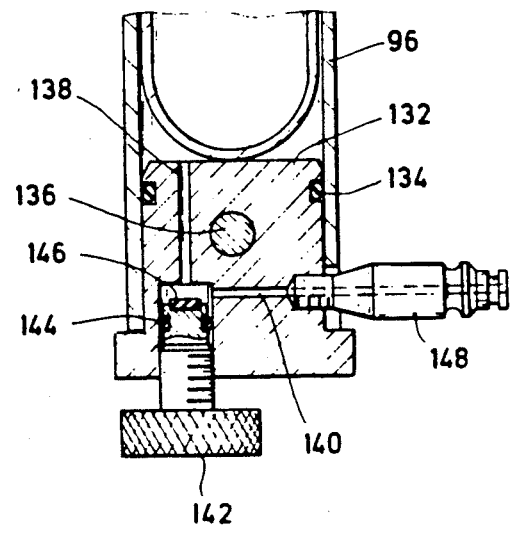

APPARATUS AND METHOD FOR ANALYZING WELL FLUID SAG

BACKGROUND OF THE INVENTION

1. Field of the Invention

The present invention addresses a problematic phenomenon in well fluids, such as drilling muds, for which the term "sag" has been coined. Sag occurs, for example, when circulation of the fluid is stopped for a period of time, e.g. when the drill string must be tripped from the well, and is caused by the resulting settling or stratification of the fluid whereby "heavy spots" develop. Sag can also involve movement or shifting of the fractions, particularly the "heavy spots," where components such as barite have become concentrated. Sag may not occur throughout an entire well, but nevertheless, its occurrence in even a small section of the well can cause the problems referred to below.

Such settling is not particularly problematic if the well is a vertical or near vertical. The magnitude of the problem is also relatively small if the well, or the section of the well in question, is nearly horizontal. However, if the well or a section thereof has a relatively high deviation angle (i.e. angle with respect to vertical), but falling well short of 90°, sag problems can become particularly severe. The advent and recent strides in extended reach drilling, which have resulted in relatively highly deviated wells, e.g. wells with deviation angles of 20° or more, has brought sag problems currently into focus in the industry.

Among the problems caused by sag phenomena are sticking of drill pipe, difficulty in re-initiating and/or maintaining proper circulation of the fluid, possible loss of circulation and disproportionate removal from the well of lighter components of the fluid.

2. Description of the Prior Art

Prior efforts to control sag phenomena have included modification of muds or drilling fluids by altering parameters such as the yield point, which were believed to affect sag. However, the basis for such variations was mainly actual field experience which, because of the inability to know with certainty precisely what is occurring downhole, involved a certain amount of guess work.

Techniques have been developed for testing and/or analyzing other properties of well fluids, in a laboratory environment, but these were not intended to analyze sag, and none of them is completely satisfactory for that purpose.

More specifically, one of these techniques was used to test for a phenomenon known as "top oil separation" in invert emulsion drilling fluids. Top oil separation does not, to the inventors' knowledge, occur in actual downhole conditions, only in laboratories and the like, but is sometimes considered a factor which should be controlled out of an excess of caution. Top oil separation does not involve the true statification of the drilling fluid which occurs in connection with sag, but merely refers to the sweating or bleeding of a relatively thin layer of pure oil to the upper surface of a volume of mud, with the remainder of mud remaining more or less homogenous. In accord with this technique, samples of the mud were placed in test tubes which were heated in an oven, whereafter the amount of oil which had separated to the top was measured. Coincidently, in at least some such procedures, the tubes were placed in the oven at an angle, simply because the length of the tubes and the size of the oven did not permit upright orientation. The result was not necessarily a measure of sag, or true stratification, which may or may not have occurred in the test. Furthermore, the numerical result was merely a quantity or percentage of oil and was not related to time.

Other systems, known as "flow loops" have been devised for studying the circulation of cuttings. While it is conceivable that such systems might be utilized to test or predict sag, because they are really intended to analyze cutting circulation, and then due to the size of typical well cuttings, it has been felt, perhaps correctly, that the test systems should be approximately "full scale." Thus, they are large, expensive, and may require a relatively high degree of skill and/or training to operate. Furthermore, the flow loops are, by nature, intended to simulate and analyze a dynamic condition, i.e. circulation, and not the static condition, when circulation is lost or stopped, which results in sag.

Other methods have been used to test the shear strength of drilling fluids using conventional rheometers. However, this neither simulates nor accurately predicts sag.

SUMMARY OF THE INVENTION

The present invention provides an apparatus and a method for simulating and analyzing sag phenonmena in well fluids wherein the results may be and preferably are expressed as a function of time, and which can be performed with a relatively simple apparatus, on a small scale, in a laboratory or even in the field. Preliminary results indicate that the method and apparatus of the present invention are not only far superior to any prior known technique, but in fact, and rather surprisingly, tests performed using the present invention have shown that the kinds of properties and or parameters which have been relied upon in the past as indicators or control features of sag phenomena are unreliable, and in some cases, irrelevant, i.e. these properties and/or parameters are not in fact related to sag in such a way that they can be reliably used to predict or control sag.

In particular, in the method of the present invention an elongate container containing a sample of a fluid to be tested is mounted at an angle with respect to vertical to simulate a given well deviation angle. A parameter of the sample which is indicative of the sag of the sample is measured.

Preferably, this parameter is measured repeatedly and more specifically continuously, over a substantial period of time, and functionally related to time.

If the container is mounted at a non-perpendicular angle to vertical, then its center of mass can serve as the aforementioned parameter. This parameter can be measured either directly or indirectly. In preferred methods, the container is so mounted on a force responsive device which provides a measureable, variable indication of the center of mass of the container, and it is that indication which is so measured.

The apparatus according to the present invention includes such a force responsive device, mounting means associated with the force responsive device for selectively mounting a body at various angles, and an elongate container means capable of mounting on the mounting means at an angle with respect to vertical.

Even more preferably, the force responsive device comprises a pivoted arm, the indication of center of mass being provided by virtue of movement of one end of the arm in a first direction, e.g. vertical.

Measuring means for measuring this indication may comprise a strain gauge connected to the aforementioned end of the arm and adapted to produce a signal which is a function of the force exerted on the strain gauge in the first direction by the arm. This signal may be received by appropriate means, functionally related to time, and the function recorded, e.g. by a chart plotter.

The preferred method and apparatus also involve subjecting the sample to heat to simulate a downhole condition, means for sealing the sample from the surrounding environment while still permitting volumetric expansion and contraction of the sample, and several salient subsystems of the apparatus.

A principal object of the present invention is to provide an apparatus and method for simulating and analyzing sag phenomena in a slant tube containing a fluid sample.

Another object of the present invention is to provide such an apparatus and method in which the results are obtained in the form of a function of time.

Still another object of the present invention is to provide such an apparatus and method in which the center of mass of the slant tube containing the sample is used as the principal variable to be functionally related to time.

Still other objects, features, and advantages of the present invention will be made apparent by the following detailed description, the drawings, and the claims.

BRIEF DESCRIPTION OF THE DRAWING

FIG. 3 is an enlarged side elevational view of one of the pivot arms of the apparatus with associated parts, including mounting means.

FIG. 4 is a detailed sectional view taken on the line 4—4 of FIG. 3.

FIG. 8 is an enlarged cross-sectional view of the container means.

FIG. 9 is a detailed cross-sectional view through one of the closure members taken on the line 9—9 of FIG. 8.

FIG. 10 is a view similar to that of FIG. 9 showing the valve in open position.

DETAILED DESCRIPTION

Figure 1:
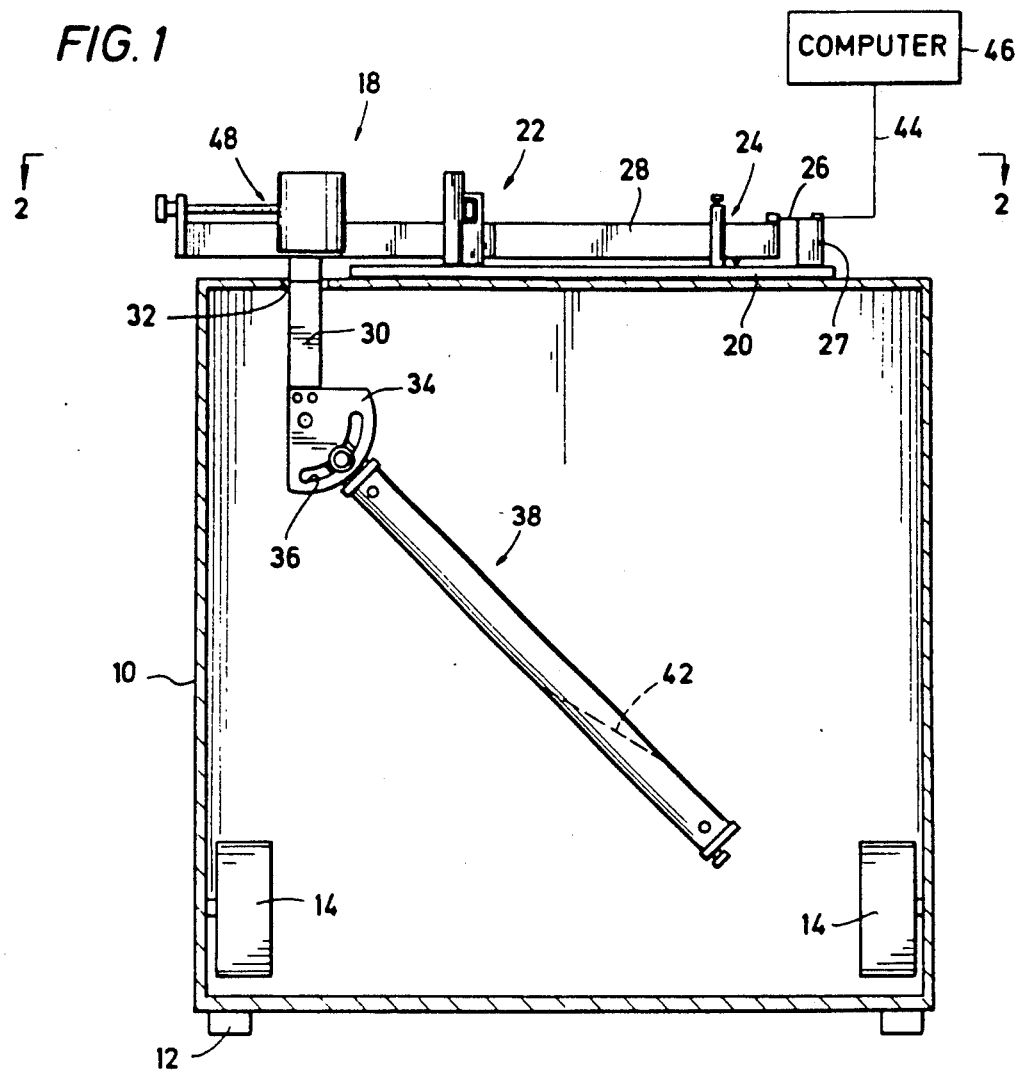
FIG. 1 is a partially schematic side view of an apparatus according to the present invention, with the oven housing shown in cross-section, and the remaining parts shown in elevation.
Figure 2:
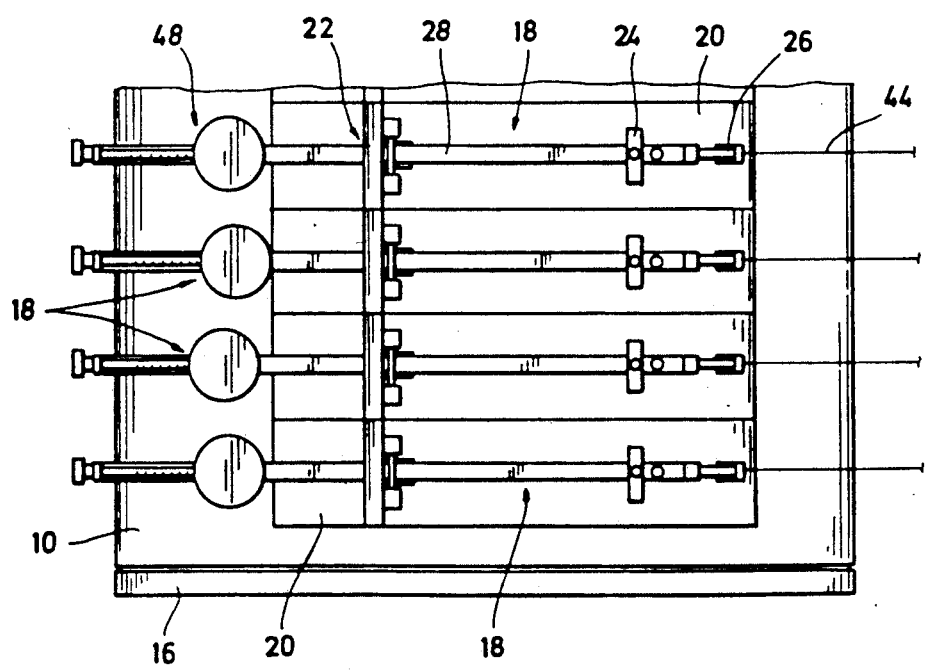
FIG. 2 is a top plan view taken on the line 2—2 of FIG. 1.
Figure 5:
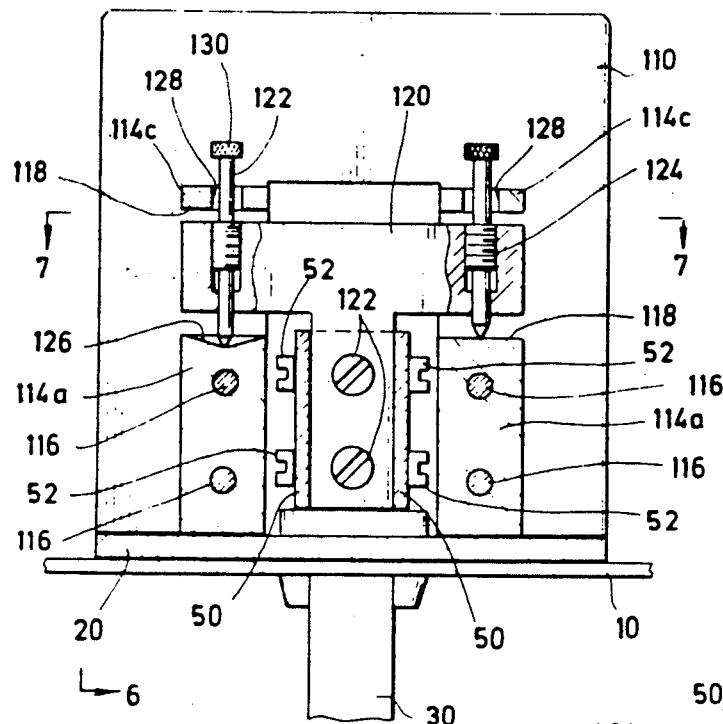
FIG. 5 is a detailed view of the pivot mechanism taken on the line 5—5 of FIG. 6.
Figure 6:
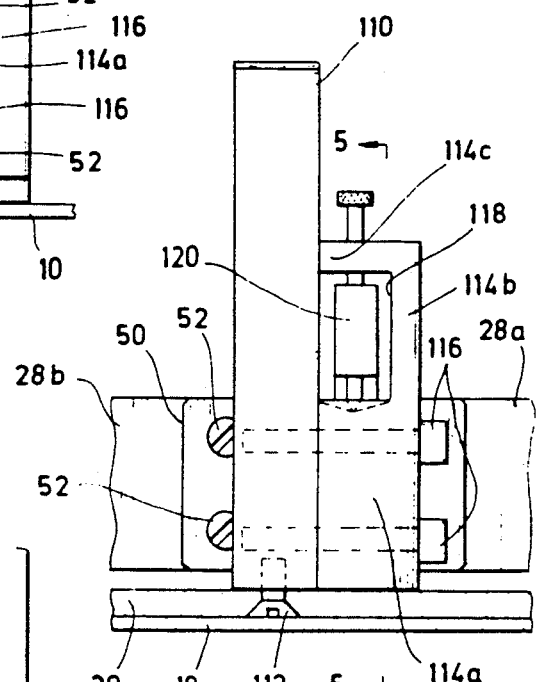
FIG. 6 is a side view of the pivot mechanism taken on the line 6—6 of FIG. 5.

FIG. 1 and FIG. 2 illustrate an exemplary embodiment of an apparatus according to the present invention. This apparatus comprises an oven having a housing 10, foot pads 12 for vibration isolation and interior heaters 14. The housing 10 also includes a door 16 permitting access to the interior of the oven.

On and in the oven 10 are arranged a battery of apparatuses 18 for handling the fluid samples to be tested. One of the apparatuses 18 will be described in detail, the others being identical. More particularly, each apparatus 18 includes a mounting plate 20 supported on the exterior of the upper wall of the oven 10. On plate 20 there is mounted a pivot mechanism 22, to be described more fully below, a limit device 24, and a strain gauge 26. Mechanism 22 mounts a pivot arm 28 for pivotal movement about a transverse horizontal axis, so that the ends of the arm 28 move in the vertical direction, which in this exemplary embodiment is "the first direction."

Adjacent the end of arm 28 distal strain gauge 26, there is attached a mounting mechanism to be described more fully below. Briefly, the mounting mechanism includes a link member 30 which depends downwardly from arm 28 and passes through an opening 32 in the upper wall of oven 10. To the lower end of link member 30 there is attached a plate 34 having an adjustment slot 36 which allows a container means 38 to be mounted on plate 34 selectively at various angles with respect to vertical. If necessary, a weight may be suspended from the free end of the container means, i.e. distal that end which is hung from plate 34, for calibration prior to testing.

It can be seen that, if the center of mass of the container means 38 should change, by virtue of sag of the fluid sample, e.g. if the contents stratify so that heavier components lie below the line 42, the moment exerted by virtue of the weight of container means 38 will change, and arm 28 will tend to pivot. Even though actual movement of arm 28 may be too small to readily observe with the naked eye, there will in fact be sufficient movement to change the force exerted on strain gauge 26 by the attached end of arm 28. Strain gauge 26 continuously measures that force over a period of time. The length of time chosen for the test should be long enough to provide a realistic prediction of the sag behavior of the sample in question in actual use. Preferably, the test should be continued until the fluid sample has stabilized, i.e. until no significant changes have occurred for some time.

Strain gauge 26 communicates by a wire 44 with a receiver 46, shown diagrammatically in FIG. 1. The receiver 46 may be, for example, a computer which receives the signal produced by strain gauge 26, which is an indication of the force being exerted by arm 28 on the strain gauge, and thus in turn an indication of the center of mass of container means 38, and functionally relates those measurements or readings to time. The resulting function is recorded in one or more appropriate media. For example, it may be recorded in the memory of the computer, and/or by a chart plotting mechanism operatively associated with the receiver 46. Some suitable means, which may be incorporated into the software for computer 46, should be used to screen out those data obtained before the desired test temperature is reached, i.e. during the initial heating of the sample.

In order to effect an initial position of arm 28, and thereby an initial reading of strain gauge 26, a balancing mechanism 48 is associated with the end of arm 28 distal strain gauge 26. This balancing mechanism, to be described more fully below, is ordinarily initially adjusted so that a relatively small force is exerted on strain gauge 26. The limit means 24 limit the vertical movement of arm 28 so as to protect the strain gauge 26 from excessive force.

Figure 7:
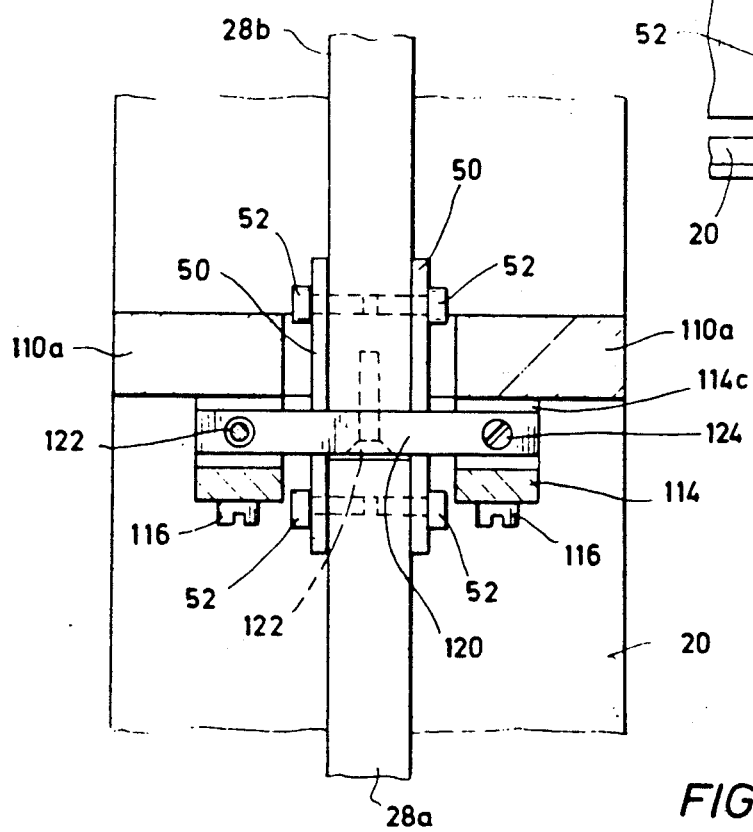
FIG. 7 is a further detailed view of the pivot mechanism taken on the line 7—7 of FIG. 5.

Turning now to FIG. 3, the arm 28 and parts associated therewith will be described in greater detail. The arm 28 is formed in two sections, 28a and 28b disposed in end-to-end relation. The adjacent ends are sandwiched between a pair of plates 50 and connected to the plates by screws 52 so that sections 28a and 28b are rigidly connected together (See FIG. 7). Section 28a is formed of a thermal insulator material, such as a suitable rigid plastic, while section 28b may be formed of a metal, such as brass.

The support plate 20 is secured to the upper wall of over 10 by screws, one of which is shown at 54. Thermal insulation (not shown) is preferably interposed between the plate 20 and the top of the oven 10. Adjacent the strain gauge 26, plate 20 has a stepped slot therethrough, elongated in the direction corresponding to the length of arm 28. This slot includes a narrow uppermost portion 56a and a wider lower portion 56b. A mounting block 27 for the strain gauge 26 can thus be adjustably secured to the plate 20 by a screw 58, the shank of which passes through portion 56a of the slot, and the head of which is received in portion 56b and abuts the step formed between portions 56a and 56b. If it is desired to move the strain gauge closer to or farther away from the adjacent end of arm portion 28a, screw 58 can be loosened, and the screw can slide along the slot 56a, 56b as the strain gauge is moved to the desire position, whereafter screw 58 is re-tightened.

The strain gauge 26 has one end sandwiched between apertured members 60, which provide a clean edge at which gauge 26 can flex. Members 60 and the engaged end of gauge 26 are secured to the end of arm section 28a by a screw 62. The other end of gauge 26 is similarly sandwiched between insulators, one of which is shown at 64, and secured to mounting block 27 by screw 66. Strain gauge 26 is adapted for producing the aforementioned variable output signal which is conveyed along wire 44.

The balancing means 48 includes a weight 68 which rests on the upper surface of arm section 28b and includes depending legs, one of which is shown at 68a, which straddle arm section 28b. Thus, weight 68 can slide along arm section 28b, and is guided in such movements by legs 68a. In order to more easily and accurately effect such movements, an adjusting screw 70 of suitable length is threaded into weight 68 parallel to the length of arm 28. The end of the screw has a reduced diameter neck which is rotatably supported, but restrained against longitudinal movement, by an upstanding plate 74 affixed to the outer end of arm section 28b by screws 76. A knob 72 integrally fixed to screw 70 is disposed on the outer side of plate 74 for engagement by the operator.

The link 30 of the mounting means is connected to arm section 28b by screws 78, countersunk in arm section 28b so as not to interfere with weight 68. Screws 78 also pass through a shim 80, which can, as a practical matter, be considered part of the mounting means, and indeed part of the link 30. Shim 80 also serves as a baffle to minimize heat loss through aperture 32.

Referring now jointly to FIGS. 3 and 4, the mounting means further comprises an adjustable link 82 having a flat, plate-like arm 82a lying in a reduced thickness area 30a of link 30 and extending angularly from link 30 beyond plate 34. Link 82 further comprises a cylindrical portion 82b at the outer end of arm 82a. Link 30, arm 82a and plate 34 have aligned bores 86, 88 and 90, respectively, the bore 88 being larger in diameter than the bores 86 and 90. In these aligned bores there is disposed a pivot pin 84 whose diameter is stepped to correspond to the diameters of the bores. Because the central step is greater, pin 84 is sandwiched between link 30 and plate 34 and thus retained in the bores as long as link 30 and plate 34 are connected together. This connection is achieved by screws 92. Arm 82a is, in turn, secured to plate 34 by the nut and bolt assembly 94, the bolt of which extends through slot 36 in plate 34. By loosening the nut and bolt assembly 94, link 82 can be pivoted about pin 84 to a desired testing angle, the movement being permitted by sliding of the bolt of assembly 94 in arcuate slot 36, the center of which is coincident with the axis of pin 84. When the desired angle has been achieved, the nut and bolt assembly 94 is tightened to maintain that angle.

The container means 38, to be described more fully below, includes an outer cylindrical casing 96 in the end of which is disposed a closure plug 98. The closure plug 98 is secured in casing 96 by a transverse pin 100 and sealed with respect to casing 96 by O-ring 102. Closure plug 98, while part of the container means, can also be considered part of the connecting means in that it cooperates with cylindrical portion 82b of the movable link to suspend the container means 38 with a frictional binding type action. More specifically, there is a cylindrical recess 98a extending axially into the center of the outer end of plug 98. Link portion 82b is sized for a sliding fit in recess 98a. When emplaced therein, as shown, the moment imposed by virtue of the weight of the container means 38, coupled with the manner in which it is suspended angularly from one end, will cause the aforementioned frictional binding effect, whereby container means 38 is suspended from the mounting means, but easily removable without disturbing the contents. It is noted that section 82b of the movable link has a notch 82c for receiving pin 100.

The limit means 24 includes means for limiting both upward and downward movement of the outer end of arm section 28a. Limit means 24 includes a saddle-like body 104 which straddles arm section 28a and is secured in any suitable manner to plate 20. It should be noted that the height of the recess in body 104 is greater than that of arm section 28a, so as to permit the desired vertical moment. However, upward movement of arm section 28a is limited by an adjustable screw 106 which extends downwardly into the recess of the body 104 for abutment with the upper surface of arm section 28a. The limit means further comprises another adjustable screw 108 threaded directly into arm section 28a and extending downwardly therefrom for abutment with plate 20 to limit downward movement of arm section 28a.

Referring now jointly to FIGS. 3 and 5–7, the pivot assembly 22 will be described in greater detail. The pivot assembly is designed to minimize friction therein, upon pivotal movement of arm 28, so as to maximize the sensitivity and accuracy of the measurements of variations in the position of arm 28 as it effects the force applied to strain gauge 26. To this end, the pivot assembly comprises two main subassemblies: a base subassembly, which in the illustrated embodiment is connected to the support 20, and a contact subassembly, connected to the arm 28, having sharp contact surface means engaging the base and defining the pivot axis for the arm 28. However, it should be appreciated that arrangements could be devised in which the contact subassembly is carried by the support, and the base subassembly carried by the pivot arm. It should also be understood that the manner of connection of the various parts, as well as their form, could be varied. In particular, that subassembly which is connected to the support can be so connected either directly or indirectly, the references herein to connection to the support being a convenient way of indicating that there is some connection between that subassembly and the stationary parts of the apparatus.

Turning now to the illustrated embodiment, the base subassembly comprises an upstanding plate-like main base member 110 having a saddle or inverted U-shaped configuration, with legs 110a straddling the arm 28 and resting on support 20. The legs 110a are connected to support 20 as by screws, one of which is shown at 112 in FIG. 6. The base subassembly also comprises a recessed base member 114 secured to one of the broad sides of member 110, referred to hereinafter as the "forward" or "front" side by screws 116. Member 114 has a generally saddle or inverted U-shaped configuration when viewed from the front. Thus, it has leg portions 114a interconnected by a bridge portion 114b. Leg portions 114a further extend rearwardly from the bridge portion 114b to abut member 112. There are also a pair of laterally spaced apart rearward projections 114c extending rearwardly from the uppermost part of bridge 114b, and also abutting member 112. Thus, between the upper and lower rearward projections on each side, respectively, of member 114, there are defined a pair of recesses 118 opening rearwardly and laterally outwardly.

The contact subassembly of the pivot mechanism includes a T-shaped carrier 120 the leg of which is secured to the end of arm section 28b by screws 122, and the arms of which are received in respective recesses 118. Each of the arms of the T-shaped carrier 120 carries a respective adjustable contact pin 122 or 124. The contact pins are arranged vertically and have sharpened lower points. They also have threaded sections, mating with threaded bores in the arms of carrier 120, so that the positions of the pins can be adjusted.

The sharp points of the two pins 122 and 124 define, with a minimum of surface engagement, and therefore a minimum of friction, the pivot axis for the arm 28. It can be seen that the axis thus defined lies horizontally and transverse to the arm to effect pivotal movement in the "first" direction defined above, i.e. a vertical direction. The upper surfaces of the rearward extensions of the leg portions 114a of member 114 define, within recesses 118, broad surfaces capable of engaging the sharp ends of the pins 122 and 124 with minimum frictional resistance to movement.

In order to resist lateral shifting of the arm 28 with respect to the support 20 and to return the pins to their proper position, e.g. if there is some displacement during setting up of a test, the upper surface of the rearward extension which engages pin 122 is provided with a shallow recess 126 which will position pin 122 in the lateral direction without engaging more than the necessary amount of surface area, i.e. without engaging more than the point of pin 122. Pins 122 and 124 also extend upwardly through oversized bores 128 in the aligned upper rearward extensions 114c of member 114, terminating in knobs 130 so as to facilitate lengthwise adjustment of pins 122 and 124 within carrier 120. The surface of member 114 which is engaged by the other pin 124 does not have to be recessed, because longitudinal movement of arm 28 is prevented by the strain gauge 26, and lateral movement of arm 28 is limited by base member 110 and body 104. The amount of lateral play permitted is less than the width of recess 126 so that, if there is some displacement, e.g. during test set up, the pin 122 will ride down the incline of recess 126 and return to its proper position.

Referring now to FIGS. 8-10, the container means 38 will be described in greater detail. It has already been mentioned that the container means includes an outer casing 96, the upper or attachment end of which is closed by a closure plug 98 retained by pin 100 which passes laterally through aligned bores in the casing 96 and the closure 98. The portions of pin 100 which are aligned with and pass through the wall of casing 96 in use are necked down or reduced in diameter as indicated at 100a. Rings (not shown) are placed in areas 100a to hold pin 100 in place until the container is pressurized. Thereafter, pins 100 are frictionally retained by virtue of the pressure urging closure 98 outwardly. Closure 98 also has a knurled outer flange 98b which overlies the edge of casing 96 for ease of emplacement and removal of closure 98.

The lower or free end of casing 96 is likewise provided with a removable sealed closure member or plug 132. Like closure 98, closure 132 is sealed with respect to casing 96 by an O-ring 134 and is provided with a knurled outer flange 138. Also, closure 132 is held in place by a pin 136 similar to pin 100, except that it includes reduced diameter end projections 136a for suspending a weight, when such is used for initial calibration.

Unlike closure 98, closure 132 does not have a large central recess corresponding to recess 98a because this closure is not used for the end of the container which is suspended from the mounting means. On the other hand, closure 132 is provided with a pressurization port system, including a valve for opening and closing that system, whereby the interior of casing 96 can be pressurized. This port system includes a lengthwise bore 138 extending completely through closure 132, and a lateral bore 140 extending from the outer diameter of closure 132 laterally inwardly to intersect bore 138 at a right angle. The outer portion of bore 138 is enlarged, and the enlarged portion includes an innermost smooth part 138a forming a seal surface, and a threaded outermost part 138b.

A valve member 142 has an outermost knurled knob 142a and a shank which extends into the enlarged portion 138a, 138b of the lengthwise port 138. Adjacent knob 142, this shank is threaded, as indicated at 142b, to mate with port section 138b. The innermost end portion 142c of the shank of the valve member carries an O-ring 144 for sealing against port section 138a as well as an end seal 146 which can seal against the shoulder formed between section 138a and the smaller diameter section of port 138 inwardly thereof.

FIG. 9 shows the valve member 142 threadedly advanced toward to engage seal 146, and it can be seen that, since port 140 communicates with port 138 outwardly of seal 146, and since the outer portion of port 138 is also sealed by O-ring 144, pressure cannot escape from the interior of casing 96 when the valve 142 is in the position of FIG. 9.

When it is desired to pressurize or depressurize the interior of the casing 96, valve member 142 can be backed away by threading outwardly to space seal 146 from the opposed shoulder of port 138 as shown in FIG. 10. For pressurizing the casing 96, the outer part of bore 140 is enlarged and threaded at 140a, and the casing is apertured at 96a, to receive a standard fitting 148.

In addition to casing 96, container means 38 also comprises a glass tube 150 disposed within casing 96.

Tube 150 can be slidably emplaced in or removed from casing 96, but there is sufficient clearance therebetween so that, when the casing 96 is pressurized in the manner just described, pressure can communicate with the open upper end of tube 150 so as to pressurize the contents of the tube.

It is, however, desirable to isolate those contents, which comprise the sample being tested, while still permitting volumetric expansion and contraction thereof, as will be induced by the pressurization and/or heating of the sample. Thus, a closure piston 152 of a free floating type is disposed in the open end of tube 150. This piston is sealed with respect to tube 150 by an O-ring 154.

For optimizing the isolation of the sample, the piston 152 is provided with a lengthwise bore 156, the outer end of which is enlarged and threaded to receive a plug 158. The drilling fluid sample can be placed in tube 150 followed by the piston 152, without plug 158. Piston 152 is forced inwardly until the operator can see the drilling fluid entering bore 156, thereby indicating that as much air as possible has been bled off therethrough. Then, plug 158 is emplaced.

Thereafter, the glass tube 150 is installed in casing 96, whose ends are closed by the closures 98 and 132. The interior of casing 96, and thus the contents of the tube 150, are then pressurized by opening the valve 142 and introducing a suitable fluid (gas or liquid) under pressure through port 140. The test pressure may be just high enough to prevent boiling of the sample at the desired test temperature, or it may be higher so as to simulate a downhole condition. When the pressure has reached the desired point, which can be determined by gauge means well known in the art, valve 142 is closed, fitting 148 is removed, and the container means 38 is ready for installation in the oven.

Movable link 82 is adjusted to the desired angle, and then its cylindrical portion 82b is installed in the recess 98a, with slot 82c receiving pin 100 and thus indexing the container means 38.

Depending on the nature of the test or analysis to be done, similar containers can be mounted on the other apparatuses 18. For example, each container might contain an identical fluid sample, but the angles at which the various containers are oriented might be varied from one apparatus 118 to the next. In another type of analysis, the angles might be identical, but the composition of the samples in the respective containers might be varied.

Next, each of the arms 28 is balanced utilizing the balancing means 48. Then, the oven 10 is closed and the heaters 14 activated to heat the contents of the containers 38 to a desired temperature. When the desired temperature is reached, if not before, the computer 146 can be engaged to begin recording the measurements continuously taken by the strain gauge 26, functionally relating these measurements to time, and recording the functional relationship. That function is known as the "sag signature" for the sample in question. The computer 46 may chart or otherwise record the sag signature. It may also integrate the sag signature, the integral being known as the "sag coefficient." One or more computers or other receivers 46 can be used to produce separate functions and records thereof for each of the apparatus 18 and to further analyze the data in any desired manner.

It can be seen that, as stratification of the contents of a container 38 occurs, the heavier components will settle toward the outer, lower end of the container 38. This alters the center of mass of that container and its contents, which in turn alters the moment placed on the mounting means by the container. This will effect minor vertical pivotal movements of the arm 28, altering the force thereof on strain gauge 26, and the signal produced by the strain gauge and analyzed by the receiver 46 will vary.

Using the method and apparatus of the invention, surprising results have already been obtained. In particular, it has been found that viscosity factors such as yield point, ten minute and ten second gel strengths, and plastic viscosity, which have previously been used either to predict and/or attempt to control sag are unreliable, and in some cases irrelevant, to the sag phenomenon. Using this apparatus and method, variations in the composition of a fluid can be tested, conveniently, on a small scale, either in a laboratory or in the field, until a mud composition which will avoid sag problems under the anticipated field conditions is tailored. Also, information generally useful in formulating drilling fluids can be gained by the use of this method and apparatus.

Various modifications of the exemplary embodiments described and illustrated herein will suggest themselves to those of skill in the art. Accordingly, it is intended that the scope of the present invention be limited only by the claims which follow.

What is claimed is:

1. A method of analyzing sag phenomena in well fluids, comprising the steps of:
   mounting an elongate container containing a sample of a fluid to be tested at an angle with respect to vertical to simulate a given well deviation angle;
   repeatedly measuring, over a period of time, a parameter of said sample which is indicative of the sag of the sample;
   and functionally relating the measurements so obtained to time.

2. The method of claim 1 further comprising recording the functional relationship.

3. The method of claim 2 further comprising integrating the functional relationship.

4. The method of claim 2 wherein the container is so mounted on a force responsive device which provides a measurable, variable indication of the center of mass of the container, and it is that indication which is so measured.

5. The method of claim 4 wherein the measuring is done continuously over said period of time.

6. The method of claim 4 further comprising subjecting the sample to heat to simulate a downhole condition.

7. The method of claim 6 further comprising subjecting the sample to pressure sufficient to prevent boiling.

8. The method of claim 6 further comprising subjecting the sample to pressure to simulate a downhole condition.

9. The method of claim 6 comprising sealing the sample from the surrounding environment.

10. The method of claim 9 comprising so sealing while permitting volumetric expansion and contraction of the sample.

11. The method of claim 6 comprising permitting volumetric expansion and contraction of the sample.

12. A method of analyzing sag phenomena in well fluids, comprising the steps of:
   mounting an elongate container containing a sample of a fluid to be tested on a force responsive device which provides a measurable, variable indication of the center of mass of the container, at an angle with respect to vertical;

holding said angle generally constant, but for small movements corresponding to changes in the center of mass of the container due to sagging of the contents of said sample, for a period of time sufficient for such sagging to occur; and measuring said indication.

13. The method of claim 12 wherein said indication is repeatedly measured over a period of time and functionally related to time.

14. An apparatus for analyzing sag phenomena in well fluids, comprising:

a force responsive device;

elongate fluid container means;

mounting means associated with the force responsive device for selectively mounting the container means on the force responsive device at various angles, and adapted, when the container means is so mounted at a given angle, to generally maintain such given angle, but for small movements corresponding to changes in the center of mass of the container means due to sagging of the contents thereof;

the force responsive device being adapted to provide a measurable, variable indication of the center of mass of the container means as affected by such sagging.

15. The apparatus of claim 14 further comprising measuring means operably associated with the force responsive device for automatically measuring said indication.

16. The apparatus of claim 15 wherein the measuring means is adapted to so measure continuously.

17. The apparatus of claim 15 further comprising means communicating with the measuring means and adapted to functionally relate the measurements from the measuring means to time and to record the functional relationship.

18. The apparatus of claim 14 wherein said force responsive device comprises a pivoted arm, said indication being provided by virtue of such small movements of one end of the arm in a first direction.

19. The apparatus of claim 18 further comprising measuring means operably associated with the one end of the arm and adapted to measure said indication.

20. The apparatus of claim 19 wherein the measuring means comprises a strain gauge connected to the one end of the arm and adapted to produce a signal which is a function of the force exerted on the strain gauge in said first direction by the arm.

21. The apparatus of claim 20 further comprising receiving means communicating with the strain gauge so as to receive said signal and adapted to functionally relate the signal to time.

22. The apparatus of claim 20 further comprising limit means adjacent the arm to limit movement of the one end in said first direction.

23. The apparatus of claim 20 further comprising:

a support on which the strain gauge is mounted; and a pivot mechanism cooperative between the support and the arm and comprising a base connected to one of the arm or the support and contact means connected to the other of the arm or the support, the contact means having sharp contact surface means engaging the base and defining the pivot axis for the arm.

24. The apparatus of claim 23 wherein the contact means comprises at least one pin, the contact surface means comprising a sharp end of the pin.

25. The apparatus of claim 24 wherein the contact means further comprises another pin spaced from the one pin in the direction of the pivot axis, and the contact surface means further comprises a sharp end of the other pin.

26. The apparatus of claim 24 wherein the sharp end of the pin is received in a recess in the base, the recess being configured to contact only the point of the sharp end of the pin.

27. The apparatus of claim 26 comprising means limiting lateral movement of the arm transverse to said first direction to an amount less than the width of the recess.

28. The apparatus of claim 27 wherein the base of the pivot mechanism is adapted to so limit lateral movement of the arm.

29. The apparatus of claim 26 comprising means limiting movement of the arm lengthwise and laterally transverse to said first direction.

30. The apparatus of claim 20 further comprising adjustable balance means associated with the arm for effecting an initial setting of the strain gauge.

31. The apparatus of claim 30 wherein the balance means comprises a weight reciprocable lengthwise of the arm.

32. The apparatus of claim 18 wherein the first direction is vertical.

33. The apparatus of claim 14 further comprising means for heating a fluid sample in the container means.

34. The apparatus of claim 33 wherein said heating means comprises an oven surrounding the container means.

35. The apparatus of claim 34 wherein the force responsive device is disposed outside the oven; and wherein the mounting means comprises link means passing movably through an opening in the wall of the oven between the container means and the force responsive device.

36. The apparatus of claim 33 further comprising pressure responsive seal means associated with the container means and adapted to permit expansion of the sample.

37. The apparatus of claim 36 wherein the container means comprises a tube having an open end; and wherein the pressure responsive seal means comprises a free-floating piston in the tube adjacent the open end and sealed with respect thereto.

38. The apparatus of claim 37 wherein the piston has a closable bleed port for bleeding air from the tube to isolate the sample.

39. The apparatus of claim 33 further comprising means for applying pressure to the sample.

40. The apparatus of claim 14 further comprising means for applying pressure to a fluid sample in the container means.

41. The apparatus of claim 40 wherein the container means comprises an elongate casing having at least one open end with a removable closure member therein, the other end of the casing also being closed; the closure member having pressurization port means therethrough and valve means for opening and closing the pressurization port means.

42. The apparatus of claim 41 wherein the container means further comprises a tube disposed within the casing for receiving the sample, the tube having one open end in pressure communicative relation to the pressurization port means, and pressure responsive seal means associated with the open end of the tube to seal between the sample and the exterior of the tube while communicating pressure within the casing to the sample.

43. The apparatus of claim 42 wherein the pressure responsive seal means is a free-floating piston in the tube adjacent the open end thereof and sealed with respect thereto.

44. The apparatus of claim 14 wherein the mounting means comprises frictional binding means cooperative between one end of the container means and the remainder of the mounting means for binding the container means in place by virtue of the moment imposed when the container means is suspended from its one end at an angle to vertical.

45. The apparatus of claim 14 wherein the container means comprises a tube with an open end for receiving a sample.

46. The apparatus of claim 45 wherein the container means further comprises an elongate casing receiving the tube.

47. The apparatus of claim 46 wherein there is a pressure responsive seal means adjacent the open end of the tube for communicating pressure between the interior and the exterior of the tube while sealing therebetween.

48. An apparatus for analyzing sag phenomena in well fluids, comprising;
 a force responsive device;
 elongate fluid container means;
 mounting means associated with the force responsive device for selectively mounting the container means on the force responsive device at various angles;
 the force responsive device being adapted to provide a measurable, variable indication of the center of mass of the container means;
 measuring means operably associated with the force responsive device for repeatedly measuring said indication; and
 means communicating with the measuring means and adapted to functionally relate the measurements from the measuring means to time and to record the functional relationship.

49. An apparatus for analyzing sag phenomena in well fluids, comprising:
 a force responsive device comprising a pivoted arm.
 elongate fluid container means;
 mounting means associated with the force responsive device for selectively mounting the container means on the force responsive device at various angles;
 the force responsive device being adapted to provide a measurable, variable indication of the center of mass of the container means by virtue of movement of one end of the arm in a first direction; and
 a strain gauge connected to the one end of the arm and adapted to produce a signal which is a function of the force exerted on the strain gauge in said first direction by the arm, the signal providing a measurement of said indication.

50. An apparatus for analyzing sag phenomena in well fluids, comprising:
 a force responsive device;
 elongate fluid container means;
 mounting means associated with the force responsive device for selectively mounting the container means on the force responsive device at various angles;
 the force responsive device being adapted to provide a measurable, variable indication of the center of mass of the container means; and
 means for heating a fluid sample in the container means.

51. An apparatus for analyzing sag phenomena in well fluids, comprising;
 a force responsive device;
 elongate fluid container means;
 mounting means associated with a force responsive device for selectively mounting the container means on the force responsive device at various angles;
 the force responsive device being adapted to provide a measurable, variable indication of the enter of mass of the container means; and
 means for applying pressure to a fluid sample in the container means.

52. An apparatus for analyzing sag phenomena in well fluids, comprising:
 a force responsive device;
 elongate fluid container means;
 mounting means associated with the force responsive device for selectively mounting the container means on the force responsive device at various angles, the mounting means comprising frictional binding means cooperative between one end of the container means and the remainder of the mounting means for binding the container means in place by virtue of the moment imposed when the container means is suspended from its one end at an angle to vertical;
 the force responsive device being adapted to provide a measurable, variable indication of the center of mass of the container means.

* * * * *